United States Patent [19]

Pohan et al.

[11] Patent Number: 5,400,790
[45] Date of Patent: Mar. 28, 1995

[54] INTRACAVITARY ULTRASOUND PROBE

[75] Inventors: Claus Pohan, Baiersdorf; Karl-Juergen Schmitt, Bamberg, both of Germany

[73] Assignee: Siemens Aktiengesellschaft, Munich, Germany

[21] Appl. No.: 125,206

[22] Filed: Sep. 23, 1993

[30] Foreign Application Priority Data

Sep. 24, 1992 [EP] European Pat. Off. ............ 92116361

[51] Int. Cl.⁶ .................................................. A61B 8/12
[52] U.S. Cl. .................. 128/662.06; 128/662.03; 128/660.10
[58] Field of Search ............. 128/660.08, 660.09, 128/660.10, 662.03, 662.06

[56] References Cited

U.S. PATENT DOCUMENTS

| | | | |
|---|---|---|---|
| 4,494,548 | 1/1985 | Buon et al. ............... | 128/660.10 |
| 4,543,960 | 10/1985 | Harui et al. .............. | 128/662.06 |
| 4,605,009 | 8/1986 | Pourcelot et al. ......... | 128/662.06 |
| 4,841,979 | 6/1989 | Dow et al. ................ | 128/660.10 |
| 4,895,158 | 1/1990 | Kawabuchi et al. ........ | 128/662.06 |
| 5,090,414 | 2/1992 | Takano ..................... | 128/662.05 |
| 5,191,890 | 3/1993 | Hileman .................... | 128/662.06 |
| 5,226,422 | 7/1993 | McKeighen et al. ........ | 128/660.08 |
| 5,255,681 | 10/1993 | Ishimura et al. .......... | 128/662.06 |

FOREIGN PATENT DOCUMENTS

| | | | |
|---|---|---|---|
| 0359546 | 3/1990 | European Pat. Off. ....... | 128/660.10 |
| 0446645 | 9/1991 | European Pat. Off. ....... | 128/662.06 |
| 2504225 | 8/1976 | Germany ..................... | 128/660.09 |

OTHER PUBLICATIONS

*Diagnostic Ultrasound, Physics, Biology and Instrumentation*, Bushong et al (1991), pp. 95–98.

Primary Examiner—George Manuel
Attorney, Agent, or Firm—Hill, Steadman & Simpson

[57] ABSTRACT

An intracavitary ultrasound probe, for producing a number of tomograms of an examination region with a common origin, includes a section adapted for introduction into a body cavity, the section having a distal end with an endpiece in which a convex transducer array is contained. The endpiece is seated in the introduction section so as to be rotatable exclusively around a single swivelling axis. The single swivelling axis is radially aligned with reference to the transducer array.

14 Claims, 3 Drawing Sheets

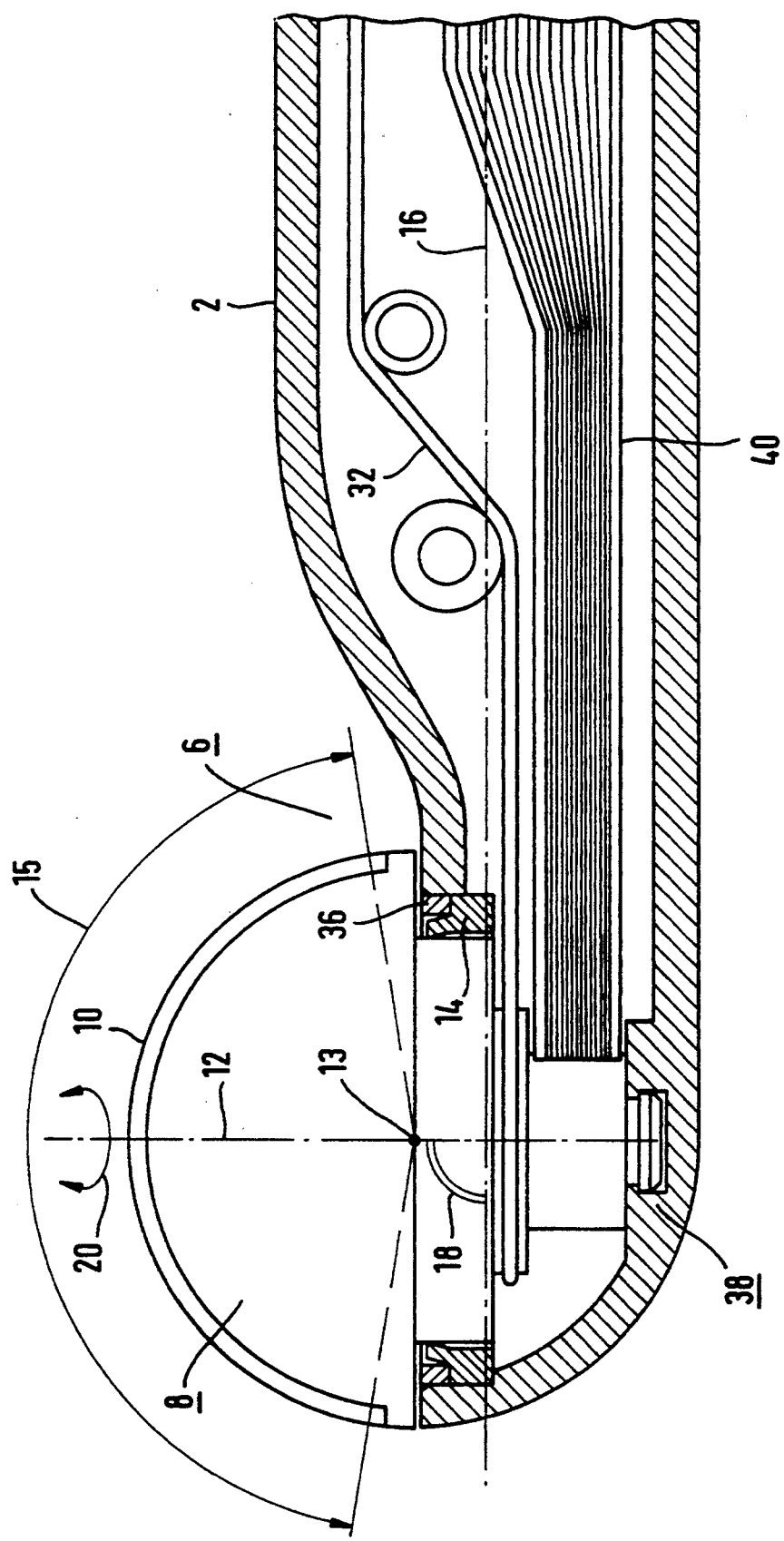

INTRACAVITARY ULTRASOUND PROBE

BACKGROUND OF THE INVENTION

1. Field of the Invention

The present invention is directed to an intracavitary ultrasound probe for producing tomograms of an examination region, of the type having a section adapted for introduction into a body cavity, the section having a distal end with an endpiece which contains a convex transducer array.

2. Description of the Prior Art

European Application 0 446 645 discloses an intracavitary ultrasound probe of the type described above for prostate examinations. The prostate probe permits scanning of the prostate with ultrasound beams proceeding from the rectum, and to produce tomograms of the prostate from the echo signals. This known ultrasound probe has a straight introduction section terminating in a distal end with a curved endpiece. The curved endpiece has an outer surface which is convexly shaped, and in which a convex transducer array is disposed. The transducer elements of the convex transducer array are activated from group-to-group in order to conduct a sector scan. The advantage of such a convex transducer array is that the ultrasound tomograms produced therewith exhibit a good graphic resolution of details in the near range of the transducer array. Moreover, convex transducer arrays offer a large scan field, so that tomograms of the entire prostate can be produced.

It would also be desirable for diagnostic and/or therapeutic purposes if the examination region could be displayed in not just one plane of section, but in a plurality of planes of section which have a common origin. A presentation of the examination region in two planes of section disposed perpendicularly relative to each other would be especially useful.

Another intracavitary ultrasound probe is disclosed in U.S. Pat. No. 4,543,960. This ultrasound probe is a transesophagal probe for cardiac examinations. The scan head of this known probe includes an interior chamber in which a phased array is rotatably mounted, in order to be able to scan in different planes. The array is rotated in the plane of the transducer elements which form the array. In the near range of the array, however, the resolution of the phased array is low, so that anatomical details in the immediate proximity of the scan head are inadequately imaged.

SUMMARY OF THE INVENTION

It is an object of the present invention to provide an intracavitary ultrasound probe having a large scan field and a good resolution in the near range, with which different tomograms of the examination region having a common origin can be produced.

The above object is achieved in accordance with the principles of the present invention in an intracavitary ultrasound probe having a section adapted for introduction into a body cavity, the section terminating in a distal end and containing a convex transducer array therein which is mounted so as to be rotatable around a single swivelling axis, the swivelling axis being radially aligned with reference to the transducer array. As a result of the radial alignment of the swivelling axis with respect to the transducer array, a plurality of tomograms in the examination region can be produced with a common origin. The anatomy of the examination region can thus be better examined. In particular, two tomograms which are disposed perpendicularly relative to each other and which have a common origin can be produced. Two tomograms having such a spatial relationship are of particularly utility for diagnostic purposes.

In an embodiment of the invention the ultrasound probe is fashioned as a prostate probe. A good resolution in the near range is achieved by employing a curved array, which permits ultrasound scanning of the prostate proceeding from the rectum.

In a further embodiment of the invention, a liquid-tight seal having a low friction resistance is disposed between the introduction section and the endpiece. Even though the ultrasound probe is provided with a protective sheath during the course of an examination, the seal prevents body fluids from penetrating into the ultrasound probe in the event the protective sheath is damaged. The seal also prevents the penetration of cleaning liquid and disinfecting agents, which may be toxic. In a further embodiment of the invention, the introduction section has a longitudinal axis and the swivelling axis intersects this longitudinal axis. The anatomy of the prostate is made especially easily accessible to an ultrasound scanning proceeding from the rectum by the lateral alignment of the scan planes.

In another embodiment of the invention, the endpiece has a dome-shaped surface, wherein the transducer array is disposed, and the swivelling axis is the axis of symmetry of this endpiece. The dome-shaped surface assures that the ultrasound probe can be introduced into a body cavity without difficulty, and also facilitates rotation of the convex transducer array in the examination position. The dome-shaped surface also provides the advantage that the radius of curvature, and thus the resolution in the near range, become as large as possible because the transducer array can be arranged within the dome-shaped surface.

In a further embodiment of the invention, a particularly large scan field is achieved by making the aforementioned surface of the endpiece a hemispherical surface. The transducer array is disposed on a longitudinal arc of a circle, this longitudinal arc having a length approximating a semicircle.

DESCRIPTION OF THE DRAWINGS

FIG. 3 is an enlarged sectional view of the distal end of a further embodiment of a prostate probe constructed in accordance with the principles of the present invention, with the swivelling axis of the transducer array being disposed at an angle of 90° relative to the longitudinal axis of the probe.

DESCRIPTION OF THE PREFERRED EMBODIMENTS

Figure 1:
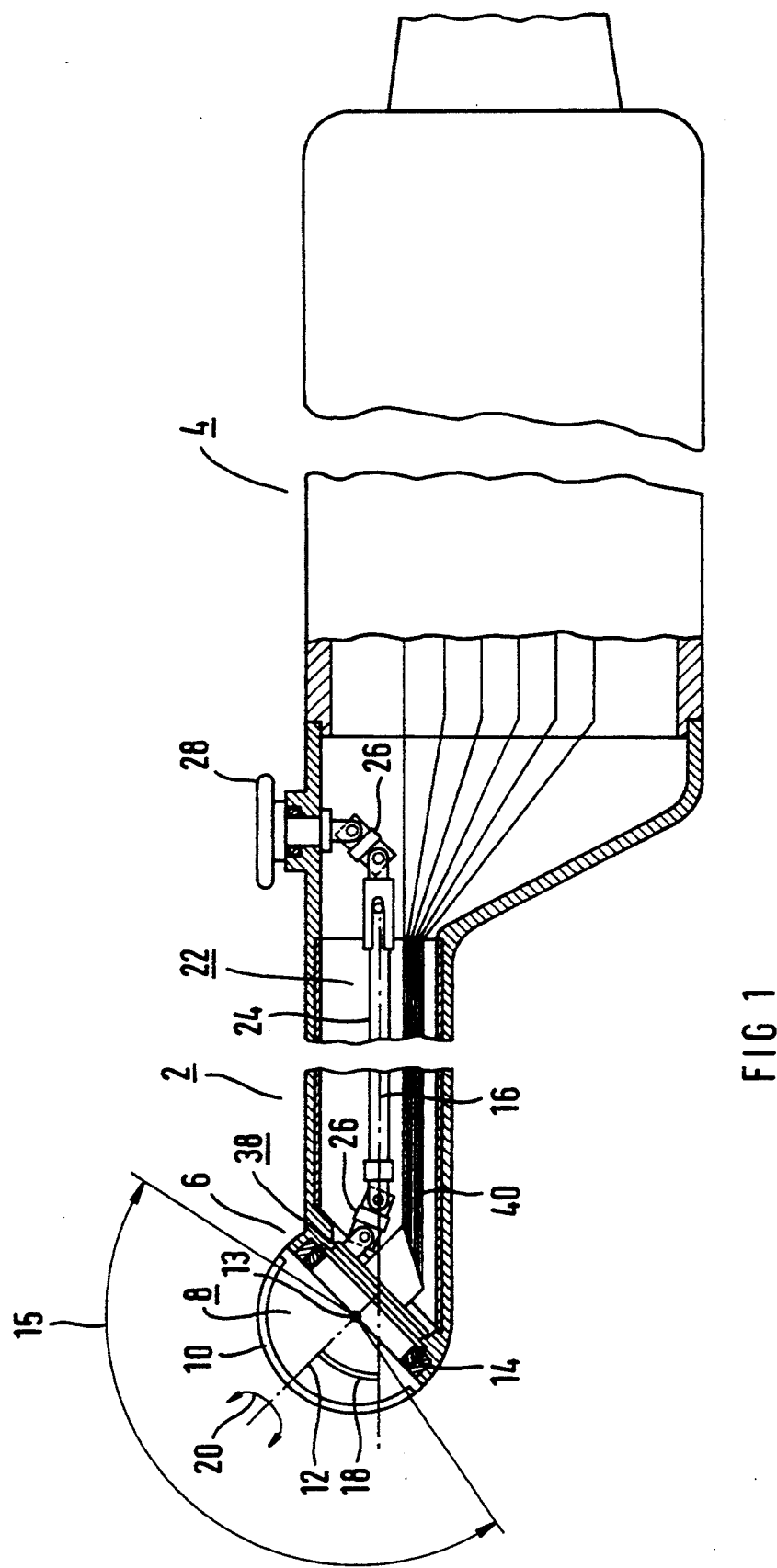
FIG. 1 shows an intracavitary ultrasound probe constructed in accordance with the principles of the present invention in longitudinal section, in the form of a prostate probe, with the swivelling axis of a convex transducer array being aligned at 45° relative to the longitudinal axis of the probe, and with means for rotating the transducer array in the form of rods connected by Cardan joints.
Figure 2:
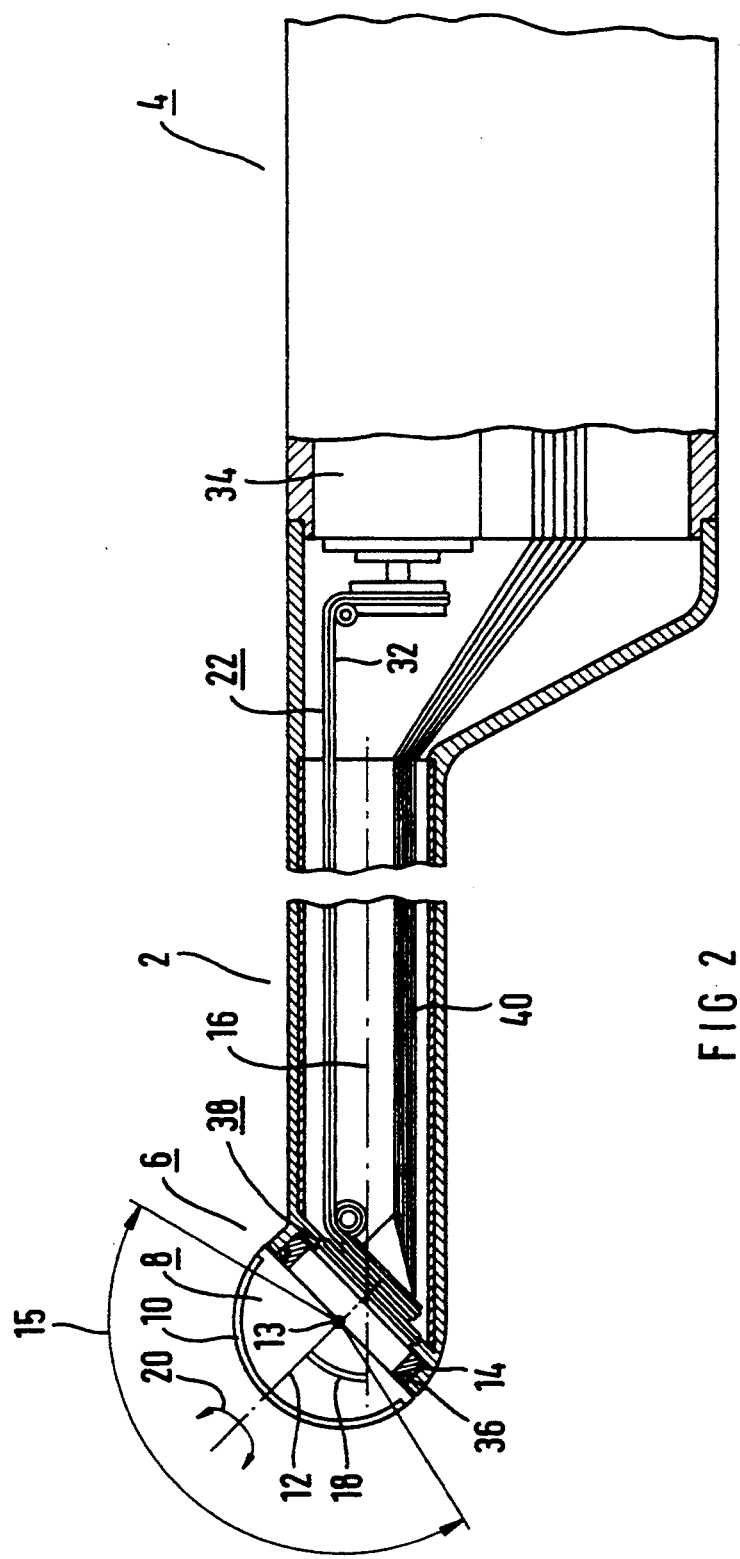
FIG. 2 is a side sectional view of a further embodiment of a prostate probe constructed in accordance with the principles of the present invention, with adjustment means formed by a cable drive.

The ultrasound prostate probe shown both in FIGS. 1 and 2 includes a straight introduction section 2, adapted for introduction into a body cavity, having a proximal end which merges into a handle 4. The introduction section 2 is approximately 150 mm long, and has a circular cross section with a diameter of 15 mm. An endpiece 8, which contains a convex transducer array 10, is disposed at the distal end 6 of the introduction section 2. The endpiece 8 is mounted in the introduction section 2 so as to be rotatable around a single swivelling axis 12. The mounting is described in greater detail with reference to FIG. 3. The swivelling axis 12 is radially and symmetrically aligned with respect to the transducer array 10. Because only one swivelling axis 12 is present, all scan planes of the transducer array 10 radiate at different angles relative to each other from a common origin 13, which is the point from which the scan rays in the scan planes appear to emanate. A liquid-tight seal 14 having a low frictional resistance is disposed between the end endpiece and the distal end 6 of the introduction section 2. The seal 14 in the embodiment of FIG. 1 is formed by an O-ring, whereas the seal 14 in the embodiment of FIG. 2 is a lip seal.

The scan field 15 of the transducer array 10 is disposed obliquely toward the front, at an angle 18 of 45°. The swivelling axis 12 therefore intersects a longitudinal axis 16 of the introduction section 2 at this angle 18.

The endpiece 8 is a hemisphere having a diameter of 20 mm, within which the transducer array 10 is disposed. The transducer array 10 is arranged on the hemispherical surface on a longitudinal arc of a circle, this longitudinal arc approximating a semicircle. The swivelling axis 12 thus coincides with the axis of symmetry of the endpiece 8. The transducer array 10 is composed, for example, of 192 elementary transducers, which are activated group-by-group for sector scanning.

The total rotation angle 20 through which the transducer array 10 can be turned is 180°. The complete volume of the prostate can thus be portrayed in tomograms. Three-dimensional data sets, from which arbitrarily oriented tomograms can be electronically formed, can thus be produced.

An adjustment mechanism 22 is provided in the interior of the introduction section 2 for rotating the endpiece 8, and thus for selecting the scan plane. In the embodiment of FIG. 1, the adjustment mechanism 22 is formed by a rod 24 having Cardan joints 26 (sometimes referred to as Hooke's joints) and a handwheel 28.

In the embodiment of the prostate probe shown in FIG. 2, the adjustment mechanism 22 is formed by a cable drive 32, having deflection rollers and which is driven by an electrical stepping motor 34. Again, the adjustment mechanism 22 rotates the transducer array 10 and thereby sets (selects) the scan plane.

In the embodiment of FIG. 3, the swivelling axis 12 is disposed perpendicularly relative to the longitudinal axis 16. For that purpose, the distal end 6 of the otherwise circular introduction section 2 is flattened parallel to the longitudinal axis 16. As in the embodiment of FIG. 2, a cable drive 32 having deflection rollers is used for rotating the endpiece 8.

The seal 14 in the embodiments of FIGS. 2 and 3 is a lip seal, which is held in a circular, milled channel at the flattened distal end 6 with a retaining ring 36.

The endpiece 8 is rotatably supported by means of a snap bearing 38, formed by a projection at the bottom of the endpiece 8 and a correspondingly shaped recess in the distal end 6. Rotatable support of the endpiece 8 is similarly implemented in the embodiments of FIGS. 1 and 2.

In all embodiments, the electrical connection of the individual transducer elements in the transducer array 10 to signal processing circuitry (not shown) is produced by means of a flexible printed circuit board 40, which extends through the interior of the introduction section 2 to the handle 4.

The introduction section 2 and the endpiece 8 are composed of disinfectable plastic, PTFE having proven suitable for the introduction section 2. Particularly low-friction bearings can be constructed using this type of plastic when other components such as, for example, the projection of the snap bearing 38, are composed of polyamide.

Although modifications and changes may be suggested by those skilled in the art, it is the intention of the inventors to embody within the patent warranted hereon all changes and modifications as reasonably and properly come within the scope of their contribution to the art.

We claim as our invention:

1. An intracavitary ultrasound probe for producing tomograms of an examination region, said probe comprising:
   an introduction section adapted for insertion in a body cavity and terminating in a distal end;
   an endpiece attached to said distal end of said introduction section;
   a convex transducer array contained in said endpiece; and
   means for mounting said endpiece relative to said introduction section for rotating said endpiece exclusively around a single swivelling axis, said single swivelling axis being radially disposed relative to said transducer array.

2. An intracavitary ultrasound probe as claimed in claim 1 wherein said introduction section is adapted for introduction into a body cavity for conducting a prostate examination.

3. An intracavitary ultrasound probe as claimed in claim 1 wherein said single swivelling axis is symmetrically disposed with respect to said transducer array.

4. An intracavitary ultrasound probe as claimed in claim 1 further comprising a liquid-tight seal having a low frictional resistance disposed between said introduction section and said endpiece.

5. An intracavitary ultrasound probe as claimed in claim 1 wherein said introduction section has a longitudinal axis, and wherein said single swivelling axis intersects said longitudinal axis.

6. An intracavitary ultrasound probe as claimed in claim 5 wherein said single swivelling axis obliquely intersects said longitudinal axis.

7. An intracavitary ultrasound probe as claimed in claim 5 wherein said single swivelling axis intersects said longitudinal axis at a right angle.

8. An intracavitary ultrasound probe as claimed in claim 1 wherein said endpiece has a dome-shaped surface in which said transducer array is contained, and wherein said single swivelling axis comprises an axis of symmetry of said endpiece.

9. An intracavitary ultrasound probe as claimed in claim 8 wherein said surface is a hemispherical surface and wherein said transducer array is disposed on a longitudinal arc of a circle of said endpiece, said longitudinal arc having a length approximating a semicircle.

10. An intracavitary ultrasound probe as claimed in claim 1 further comprising an adjustment mechanism extending through said introduction section and engaging said endpiece for rotating said endpiece around said single swivelling axis.

11. An intracavitary ultrasound probe as claimed in claim 10 wherein said adjustment means comprises a rod with Cardan joints at opposite ends thereof, one end of said rod being connected to said means for mounting and the other end of said rod being connected to means for rotating said rod.

12. An intracavitary ultrasound probe as claimed in claim 11 wherein said means for rotating said rod comprises an externally accessible wheel.

13. An intracavitary ultrasound probe as claimed in claim 10 wherein said adjustment mechanism comprises a cable drive having deflection rollers, and means for rotating a cable around said deflection rollers.

14. An intracavitary ultrasound probe as claimed in claim 13 wherein said means for rotating said cable comprises an electrical stepping motor.

* * * * *